United States Patent [19]  [11] 4,078,023
Lippsmeier et al.  [45] Mar. 7, 1978

[54] PRODUCTION OF O,O-DIALKYLTHIONOPHOSPHORIC ACID CHLORIDES

[75] Inventors: Bernd Lippsmeier; Hilmar Roszinski, both of Knapsack; Hans-Werner Stephan, Cologne-Klettenberg, all of Germany

[73] Assignee: Hoechst Aktiengesellschaft, Frankfurt am Main, Germany

[21] Appl. No.: 717,086

[22] Filed: Aug. 24, 1976

[30] Foreign Application Priority Data

Aug. 28, 1975  Germany .................. 2538310

[51] Int. Cl.² ............................. C07F 9/20
[52] U.S. Cl. ............................. 260/986
[58] Field of Search .................. 260/986, 960

[56] References Cited

U.S. PATENT DOCUMENTS

| 3,089,890 | 5/1963 | Chupp et al. | 260/986 X |
|---|---|---|---|
| 3,502,750 | 3/1970 | Anglaret et al. | 260/986 |
| 3,794,703 | 2/1974 | Beck et al. | 260/986 X |
| 3,836,610 | 9/1974 | Diveley | 260/986 |
| 3,887,659 | 6/1975 | Matsubara et al. | 260/986 |
| 3,897,523 | 7/1975 | Sorstokke | 260/986 |

FOREIGN PATENT DOCUMENTS

| 1,801,432 | 4/1973 | Germany | 260/960 |
|---|---|---|---|
| 1,191,369 | 4/1965 | Germany | 260/960 |
| 1,211,170 | 2/1966 | Germany | 260/960 |

*Primary Examiner*—Richard L. Raymond
*Attorney, Agent, or Firm*—Connolly and Hutz

[57] ABSTRACT

O,O-dialkylthionophosphoric acid chlorides are produced by chlorinating a dialkyldithiophosphoric acid in two stages. In the first stage, the acid is reacted with chlorine in a molar ratio of 1:1.15 to 1:1.50, resulting sulfur is separated, the liquid phase is admixed with a distilled product of a previous batch chlorinated in the second stage and with a further 0.25 to 0.7 mol of O,O-dialkyldithiophosphoric acid per mol of acid initially used, and desirable final product is distillatively separated from said mixture. In the second stage, the distillation residue of the first stage is reacted with a total proportion of 0.9 to 1.0 mol of chlorine per mole of acid initially used, precipitated sulfur is separated from the second stage chlorination product, the liquid phase is distilled off, and resulting distillate is recycled to the first chlorination stage.

9 Claims, No Drawings

PRODUCTION OF O,O-DIALKYLTHIONOPHOSPHORIC ACID CHLORIDES

The present invention relates to a process for making O,O-dialkylthionophosphoric acid chlorides of the general formula:

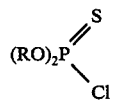

in which R stands for an alkyl radical having from 1 to 6 carbon atoms, wherein a suitable O,O-dialkyldithiophosphoric acid is reacted with chlorine and precipitating sulfur is separated from the reaction product.

Various processes (cf. German Pat. Nos. 1,191,369 and 1,211,170 and U.S. Pat. No. 3,089,890) for making O,O-dialkylthionophosphoric acid chlorides by reacting an O,O-dialkyldithiophosphoric acid with gaseous chlorine have already been described.

Depending on the particular process selected for making O,O-dialkylthionophosphoric acid chlorides, $S_2Cl_2$ or sulfur or a mixture thereof is invariably obtained as a by-product. These products which are incidentally highly contaminated are technically and commercially difficult to utilize or destroy under ecologically beneficial conditions. In this respect, some progress has been achieved by the process described in German Pat. No. 1,801,432.

This latter patent describes a process permitting very pure O,O-dialkylthionophosphoric acid chlorides to be produced in high yields, wherein a reaction mixture containing an O,O-dialkylthionophosphoric acid chloride and having been obtained by reacting 2 mols of an O,O-dialkyldithiophosphoric acid with 3 mols of chlorine, is admixed at temperatures of 0 to 75° C with a further mol of O,O-dialkyldithiophosphoric acid and then distilled. The distillation residue which is purified by freeing it from precipitated sulfur is used once again in effecting the reaction of O,O-dialkyldithiophosphoric acid with chlorine. Failing this, 1 mol of O,O-dialkyldithiophosphoric acid would be lost per batch. This however is disadvantageous in respect of the following two points: The fact that the distillation residue is passed several times through the chlorinating stage inevitably effects undesirable side reactions, which occur to an increasing extent and which adversely affect the composition, quality and properties both of the desired final product and of the sulfur residue, and it also effects the formation of a continuously increasing quantity of liquid reaction residue. In other words, it is impossible for high-grade, O,O-dialkylthionophosphoric acid chlorides to be separated in good yields, once the process has been repeated not more than 3 to 4 times.

It is therefore an object of the present invention by improving the method described in German Pat. No. 1,801,432 to provide a process for making O,O-dialkylthionophosphoric acid chlorides, which enables the final product to be obtained in high yields and the inevitable by-products to be obtained in the form of material being extensively utilizable under ecologically more beneficial conditions than in the above known process.

The present invention now provides a process for making O,O-dialkylthionophosphoric acid chlorides of the general formula

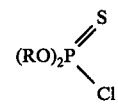

in which R stands for an alkyl radical having from 1 to 6 carbon atoms, wherein a suitable O,O-dialkyldithiophosphoric acid is reacted with chlorine and precipitating sulfur is separated from the reaction product, which process unexpectedly enables the above object to be achieved and which comprises: chlorinating the respective dialkyldithiophosphoric acid in two stages, the first stage comprising reacting the acid with chlorine in a molar ratio of 1 : 1.15 to 1 : 1.50, separating resulting sulfur, admixing the liquid phase with a distilled product of a previous batch chlorinated in the second stage and with a further 0.25 to 0.7 mol of O,O-dialkyldithiophosphoric acid per mol of acid initially used, and distillatively separating desirable final product from said mixture; and the second stage comprising reacting the distillat-ion residue of the first stage with a total proportion of 0.9 to 1.0 mol of chlorine per mol of acid initially used, separating precipitated sulfur from the second stage chlorination product, distilling off the liquid phase, and recycling resulting distillate to the first chlorination stage.

The distillation should preferably be effected under vacuum.

Further preferred features of the present process provide for the first stage chlorination to be effected at temperatures of 30° to 80° C, preferably 55° to 75° C, and for chlorine diluted with nitrogen in a molar ratio of 1 : 1 to be used in the first chlorination stage. This prevents the resulting alkylthionophosphoric acid chloride to undergo further chlorination to the corresponding dichloride.

In accordance with a further advantageous feature of the present process, the first stage chlorination is effected for as long as necessary for the resulting chlorination product to become rendered turbid by precipitating sulfur, the chlorination product is allowed to stand for a period of 15 to 30 minutes with the resultant formation of two liquid phases which are separated from one another, the lower layer being sulfur.

Still further advantageous features of the present process provide for the liquid phase separated from sulfur in the first chlorination stage to be mixed with distillate coming from the second distillation stage, and to be mixed with a supplementary proportion of acid at temperatures of 40° to 70° C, preferably 55° to 65° C, for the second chlorination stage to be effected at temperatures of 50° to 80° C, and for chlorine diluted with nitrogen in a molar ratio of 1 : 2 to be used in the second chlorination stage.

Undesirable side reactions which impair the composition, quality and properties of the desired final product can be avoided by using, as the starting material, an O,O-dialkyldithiophosphoric acid having been made by suspending $P_2S_5$ in O,O-dialkyldithiophosphoric acid, admixing the resulting suspension with 3.9 to 4.0 mols of an alcohol, per mol of $P_2S_5$, with agitation at temperatures of 50° to 110° C, and separating unreacted $P_2S_5$ from the reaction product.

The process of the present invention differs basically from, and compares very favorably with, the prior art methods in that the chlorination is effected separately in two stages. The mild conditions used and the ratio of chlorine to dithiophosphoric acid selected in the present process substantially prevent the O,O-dialkylthionophosphoric acid chloride formed from becoming further chlorinated to the dichloride (ROP(S)Cl$_2$) and thiophosphoryl chloride (P(S)Cl$_3$), inasmuch as the approximately 20 to 25% excess of chlorine, which has to be used in the first chlorination stage so as to obtain high yields, is substantially converted to disulfur dichloride which is used in the second stage for chlorinating a further quantity of O,O-dialkyldithiophosphoric acid. In other words, almost the entire theoretically necessary quantity of chlorine goes into the desired final product.

In addition to this, the step of recycling the distillate coming from the second chlorination stage to the first stage and the subsequent addition of a further quantity of O,O-dialkyldithiophosphoric acid on the one hand, and the second chlorination stage on the other hand enable intermediate by-products, e.g. disulfur dichloride, bis-(dialkoxythiophosphoryl)-disulfide, and (dialkoxy-thiophosphoryl)-sulfenyl chloride, to be either quantitatively used for effecting the chlorination, or to be completely converted to desirable final product. A further considerable advantage resides in that disulfur dichloride which is formed can be disposed of without the need to use any additional process step or auxiliary chemical agent.

The process of the present invention also compares favorably with the prior art methods, e.g. with that disclosed in German Pat. No. 1,801,432, in respect of the following points: The residue can readily and quantitatively be separated by simple phase separation in the various processing stages into its constituents, which are solid or liquid at room temperature, and the latter can be recycled, if desired. Sulfur, for example, may be recycled to the P$_2$S$_5$-production stage.

It is a further advantageous effect of the present process that the distillation of the second stage chlorination product entails the formation of a considerably less important quantity of residue than the prior art methods, wherein the desired final products are recovered by distillation. In clear contrast with the residue which is obtained in the prior art methods, the residue obtained in the present process remains liquid even at room temperature, readily separable, conveyable (by means of a pump) if treated thermally, and it does not tend to polymerize or undergo uncontrollable decomposition (explosion).

A still further feature in which the present process distinguishes over the prior art methods resides in the use of an O,O-dialkyldithiophosphoric acid which is prepared by suspending P$_2$S$_5$ in pre-prepared acid without any alcohol in excess or any additional solvent. This definitely inhibits the formation of by-products, which are very difficult to remove, such as those formed by chlorination or oxidation of alcohol in excess, e.g. the formation of dichloroacetaldehyde diethyl acetate if ethanol is used. It is a further desirable effect that the formation of extremely toxic triesters is practically avoided in the present process.

In summary, the present process enables high grade products to be produced in high yields under ecologically highly beneficial conditions.

EXAMPLE 1:

Production of O,O-dimethylthionophosphoric acid chloride. 162 g of crude O,O-dimethyldithiophosphoric acid was admixed with agitation and under nitrogen as a protective gas with 537.45 g (2.42 mol) of phosphorus pentasulfide. The resulting mixture was stirred as intensively as possible and 310.94 g (9.69 mol) of methanol was metered thereinto within 1 hour at 90° C.

The molar ratio of phosphorus pentasulfide to methanol was 1 : 4. Once the methanol had been added, the whole was allowed to react for a further 10 to 15 minutes at the temperature indicated. Hydrogen sulfide which was found to have been evolved escaped in gas form, under these conditions. Minor proportions of unreacted phosphorus pentasulfide, if any, were filtered off. Altogether 912 g of crude O,O-dimethyldithiophosphoric acid, of which 162 g was left in the reactor for the preparation of a new batch therein, was obtained under the conditions described. The crude acid so made contained 86 weight% of dimethyldithiophosphoric acid. Next, 450 g of the crude acid was reacted in the first chlorination stage within 85 minutes and with agitation with 255 g (3.59 mol) of chlorine gas diluted with nitrogen in a molar ratio of 1 : 1.

The chlorination temperature was maintained at 55° C by cooling. Slight turbidity in the batch indicated that the chlorination was complete. Next, the chlorination batch was admixed at 45° to 50° C first with 205 g of distillate coming from the second chlorination stage ("final chlorination stage") and then with 300 g of crude O,O-dimethyldithiophosphoric acid. The resulting reaction mixture was delivered to a thin film evaporator, distilled under a pressure of 5 mm Hg at 44° to 45° C and thereby separated into 624 g (3.89 mol) of O,O-dimethylthionophosphoric acid chloride and 457 g of a liquid residue. The liquid residue was introduced into the "final chlorination stage" and post-chlorinated at 50° to 55° C over a period of 21 minutes with 63.3 g (0.89 mol) of gaseous chlorine diluted with nitrogen in a molar ratio of 1 : 2. After the post-chlorination was terminated, the material was allowed to stand for 60 minutes at 53° C and 163 g of liquid sulfur began to separate which was removed by phase separation, while the upper phase was vacuum-distilled under 5 mm Hg at 42° to 45° C. 205 g yellow distillate which was recycled to the first chlorination stage was obtained. The remaining liquid distillation residue (122.3 g) was easy to handle and was removed.

In the process described, altogether 1.10 mol of chlorine was used per mol of dithiophosphoric acid, based on the O,O-dimethyldithiophosphoric acid present in the crude acid, or 0.95 mol of chlorine, based on the crude acid. O,O-dimethylthionophosphoric acid chloride was obtained in a yield of 96.4%, based on the O,O-dimethyldithiophosphoric acid present in the crude acid. The yield, based on phosphorus pentasulfide, was 80.3% (cf. Example 1 of German Pat. No. 1,801,432, wherein the yield is 76.4%, based on P$_2$S$_5$). The O,O-dimethylthionophosphoric acid chloride so obtained was colorless, completetly free from disulfur dichloride and methylthionophosphoric acid dichloride, and had a purity of 97 to 98%, determined by gas-chromatography.

EXAMPLE 2:

115 g of a 90 weight% O,O-diethyldithiophosphoric acid was placed in an agitator-provided reactor and 377.7 g (1.7 mol) of phosphorus pentasulfide was stirred thereinto under inert gas (N₂). The resulting mixture was stirred as intensively as possible and 305.4 g (6.63 mol) of ethyl alcohol was metered thereinto within 75 minutes at 90° C to 100° C.

The molar ratio of phosphorus pentasulfide to ethyl alcohol was 1 : 3.9 (2.5 weight% of alcohol deficiency). Once the etyl alcohol had been added, the whole was allowed to react for a further 10 minutes at 95° C. Evolved hydrogen sulfide was found to have been completely removed. Minor proportions of unreacted phosphorus pentasulfide, if any, were filtered off. Altogether 708 g of crude O,O-diethyldithiophosphoric acid, of which 115 g was left in the reactor for the preparation of a new batch therein, was obtained under the conditions described. The crude acid so made contained 90 weight% of diethyldithiophosphoric acid.

Next, 450 g of the crude acid was reacted in the first chlorination stage within 77 minutes and with thorough agiation with 198.8 g (2.8 mol) of chlorine gas diluted with nitrogen in a molar ratio of 1 : 1.

The chlorination temperature was maintained at 70° C by slight cooling. Slight turbidity in the batch caused by precipitating sulfur indicated that the chlorination was complete. The material was allowed to stand for 20 minutes at 60° C, and the sulfur residue (11 g = 14.1 weight% of the overall sulfur residue; 90 weight% of S) was removed as the dense liquid phase by phase separation. Next, the chlorination batch was admixed at the same temperature first with 123 g of distillate coming from the "final chlorination stage" and then with 143 g of O,O-diethyldithiophosphoric acid. The resulting reaction mixture was delivered to a thin film evaporator, distilled under a pressure of 4.5 mm Hg at 57° to 58° C and thereby separated into 546 g (2.89 mol) of O,O-diethylthionophosphoric acid chloride and 256 g of a liquid residue. The liquid residue was introduced into the "final chlorination stage" and post-chlorinated at 70° to 72° C over a period of 14 minutes with 35.75 g (0.5 mol) of gaseous chlorine diluted with nitrogen. After having been allowed to stand for 60 minutes at 60° C, the material was freed by phase separation from 69.5 g of a liquid sulfur residue and then vacuum-distilled under 2 mm Hg at 41° to 42° C, 123 g of yellow distillate which was recycled to the first chlorination stage was obtained. The remaining liquid distillation residue (86 g) was easy to handle and was removed.

In the process described, altogether 1.15 mol of chlorine was used per mol of crude O,O-diethyldithiophosphoric acid present in the crude acid, or 1.03 mol of chlorine, based on the crude O,O-diethyldithiophosphoric acid. O,O-diethylthionophosphoric acid chloride was obtained in a yield of 101 weight%, based on the O,O-diethyldithiophosphoric acid present in the crude acid. The yield, based on phosphorus pentasulfide, was 85.1%. The product so obtained was colorless, completely free from disulfur dichloride, almost free from sulfur-containing triesters, and had a purity of 97 to 98%, determined by gas-chromatography.

The product yields and the high-grade products obtained by the present process evidence that the by-products and impurities contained in a crude acid, which is prepared in the manner hereinabove described, are to a good deal additionally convertible to desirable O,O-dialkylthionophosphoric acid chlorides.

We claim:
1. In the process for making O,O-dialkythionophosphoric acid chlorides of the formula:

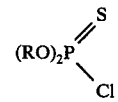

wherein R is alkyl of 1–6 carbons and wherein a suitable O,O-dialkyldithiophosphoric acid is reacted with chlorine and precipitated sulfur is separated from the reaction product, the improvement which comprises chlorinating the dialkyldithiophosphoric acid in two stages, the first stage comprising reacting the acid with chlorine in a molar ratio of said acid to chlorine of 1 : 1.15 to 1 : 1.50 for as long as necessary for the resulting chlorination product to become rendered turbid by precipitating sulfur, allowing the chlorination product to stand for 15–30 minutes with the resultant formation of two liquid phases the lower of which is sulfur, separating the said sulfur, admixing the remaining liquid phase with a distilled product of a previous batch chlorinated in the second stage and admixing it with a further 0.25 to 0.7 mole of O,O-dialkyldithiophosphoric acid per mole of acid initially used, and distillatively separating desirable final product from said mixture, the second stage comprising reacting the distillation residue of the first stage with a total proportion of 0.9 to 1.0 mole of chlorine per mole of acid initially used, separating precipitated sulfur from the second stage chlorination product, distilling off the liquid phase, and recycling the resulting distillate to the first chlorination stage.

2. The process as claimed in claim 1, wherein the first stage chlorination is effected at temperatures of 30° to 80° C.

3. The process as claimed in claim 2, wherein the first stage chlorination is effected at temperatures of 55° to 75° C.

4. The process as claimed in claim 1, wherein the first stage chlorination is effected with chlorine gas diluted with nitrogen in a molar ratio of 1 : 1.

5. The process as claimed in claim 1, wherein the liquid phase separated from sulfur in the first chlorination stage is mixed with distillate coming from the second distillation stage and with a supplementary proportion of acid at temperatures of 40° to 70° C.

6. The process as claimed in claim 5, wherein the mixing operation is effected at temperatures of 55° to 65° C.

7. The process as claimed in claim 1, wherein the second step chlorination is effected at temperatures of 50° to 80° C.

8. The process as claimed in claim 1, wherein the second stage chlorination is effected with chlorine gas diluted with nitrogen in a molar ratio of 1 : 2.

9. The process as claimed in claim 1, wherein the O,O-dialkyldithiophosphoric acid used as starting material is an acid having been made by suspending P₂S₅ in O,O-dialkyldithiophosphoric acid, admixing the resulting suspension with 3.9 to 4.0 mol of an alcohol, per mol of P₂S₅, with agitation at temperatures of 50 to 110° C, and separating unreacted P₂S₅ from the reaction product.

* * * * *